United States Patent [19]

Stasz et al.

[11] 4,145,925
[45] Mar. 27, 1979

[54] DIGITAL LIQUID VELOCITY MEASURING SYSTEM

[75] Inventors: Peter Stasz, Minneapolis, Minn.; George H. Fathauer, Mesa, Ariz.

[73] Assignee: Medtronic, Inc., Minneapolis, Minn.

[21] Appl. No.: 867,950

[22] Filed: Jan. 9, 1978

[51] Int. Cl.$^2$ .............................................. G01F 1/66
[52] U.S. Cl. ............................. 73/194 A; 128/2.05 F; 128/2.05 Z
[58] Field of Search ................ 73/194 A; 128/2.05 F, 128/2.05 Z

[56] References Cited

U.S. PATENT DOCUMENTS

| 3,741,014 | 6/1973 | Tamura | 73/194 A |
| 4,048,853 | 9/1977 | Smith et al. | 73/194 A |

*Primary Examiner*—Charles A. Ruehl
*Attorney, Agent, or Firm*—R. Lewis Gable; Joseph F. Breimayer

[57] ABSTRACT

There is disclosed a liquid velocity measuring apparatus comprising an actuable generator for providing a relatively high frequency signal to a transmitting transducer for directing an ultrasonic wave into a conduit through which liquid is directed. A receiver transducer is disposed to receive the acoustical wave as reflected from the liquid, and to provide an output signal to be amplified and demodulated to provide a train of high frequency pulses, the frequency of which is indicative of the velocity of the liquid directed through the conduit. The train of pulses is applied to a counter and a decoder for respectivey counting and decoding the pulses to provide a signal to a display whereby a digital indication of the liquid velocity is given. Further, a timing circuit is provided for enabling the generator, the counter and the decoder for a first, relatively short period of time, made dependent upon the cross-sectional area (or diameter) of the conduit through which the liquid is directed, and for energizing the display for a second, relatively long period of time to permit reading of the display.

3 Claims, 4 Drawing Figures

DIGITAL LIQUID VELOCITY MEASURING SYSTEM

CROSS REFERENCE TO RELATED APPLICATION

Reference is made to co-pending, commonly assigned application Ser. No. 798,670, entitled "LIQUID VELOCITY MEASURING SYSTEM", and filed May 19, 1977 in the names of Peter Stasz and Floyd R. Patten, which application is incorporated herein by reference.

BACKGROUND OF THE INVENTION

1. Field of the Invention

This invention relates to systems for measuring liquid velocity and in particular for measuring blood velocity on backscatter Doppler principles.

2. Description of the Prior Art

It is known to use ultrasonic devices for measurement of the speed of a liquid flow in general. These devices, most of which use two transducers, or sometimes a single transducer, use the Doppler effect. Devices are also known which apply the same principle to blood flow rate measurement. The known devices are speed meters; see particularly the articles by D. L. Franklin and collaborators in "*The American Journal of Medical Electronics*", 1st term 1966, pages 24–28, and "*IRE Transactions on Bio-medical Electronics*", January 1962, pages 44–49. As shown in FIG. 1, such ultrasonic devices typically included an ultrasonic transducer illustratively in the form of a crystal 14' that is energized by a generator 12' to emit ultrasonic waves into a conduit 24', whereby it is reflected by the liquid directed therethrough to be sensed by a detector, typically in the form of a crystal 18', the output of which is connected to a receiver 20'. The receiver 20', as will be explained below, detects the received Doppler signal which contains the velocity information. In the particular illustrative context of this invention, such principles are used to measure the velocity of blood as would be directed through a conduit external of the patient's body. Illustratively, it is contemplated that a heart assist machine would be used to aid the patient's heart or a dialysis machine be used to clean a patient's kidneys, and that the blood flow through such machines could be measured in accordance with the teachings of this invention.

The practical application of the Doppler backscatter principle consists of transmitting an ultrasonic beam into the medium whose velocity one wishes to measure and to compare the original frequency with the received shifted frequency. To retrieve the velocity information, a comparison of the scattered signal frequency with the original frequency is made by the receiver 20'. The difference in frequency is related to the flow velocity of the medium. Since the medium is flowing generally in a conduit of known dimension, the velocity information can be translated into total flow rate.

There are two basic aspects to this phenomena; the particle size can be larger than the wavelength of the transmitting ultrasound or it can be smaller, therefore acting as a point scatterer. It is noted that the red cells of blood have a typical diameter of 8 μm, thickness of 2 μm, with the wavelength of the 3.13 MHz ultrasonic beam being approximately 480 μm in blood. In the case of red cells, the cell is smaller than the wavelength of the beam and the cell is set into motion and becomes a secondary emitter acting as a point source.

The envelope of the received signal represents the heterodyne coupling of the transmitted carrier with the backscattered signal whose normal frequency has been shifted by the Doppler phenomena. This signal then is amplified, demodulated, audio amplified, processed and displayed as flow rate by the receiver 20', as shown in FIG. 1. The shift in frequency is due to the relative motion of the object with respect to the transmitter and receiver. The frequency shift due to motion of the particle with respect to the transmitter is:

$$f_1 = f_c \frac{V_O - V \cos \theta}{V_O} \quad (1)$$

where $f_1$ = Frequency of the forced particle oscillation
$V_O$ = Ultrasound velocity in medium
$V$ = Particle velocity
$O$ = Angle between the ultrasound and the velocity vector
$f_c$ = Ultrasonic carrier frequency The frequency shift due to motion of the particle with respect to the receiver is:

$$f_2 = f_1 \frac{V_O}{V_O + V \cos \theta} \quad (2)$$

where $f_1$ = Frequency of the forced particle oscillation
$f_2$ = New frequency as measured at the receiver V, $V_O$ as indicated above Combining (1) and (2), the total Doppler shift may be expressed as:

$$f = (f_c - f_1) + (f_1 - f_2) = f_c - f_2 \quad (3)$$

$$f = f_c \left( 1 - \frac{V_O - V \cos \theta}{V_O + V \cos \theta} \right) \quad (4)$$

The formula can be expanded in a series and only the most important term taken when $V_O$ (1500 m/sec) >> V << (1.5 m/sec at 10 L/minute), to provide the expression:

$$f = \frac{2 V f_2 \cos \theta}{V_O} \quad (5)$$

This is the general formula used in the backscatter Doppler flowmeter design. This signal is difficult to detect since the signal amplitude at this shifted frequency is small and becomes swamped by the direct coupled ultrasonic carrier frequency. Fortunately, the direct radiated ultrasonic wave received is added with the backscatter signal in the crystal 18' producing an amplitude modulated signal that retains all the basic information as indicated by formula (5). The receiving crystal 18' converts the ultrasonic energy back into an electrical signal. The amplitude modulated signal, at microvolt levels, is RF amplified, detected, audio amplified, processed and displayed as flow information.

In the above-referenced application, entitled "Liquid Velocity Measuring System", there is described a liquid and in particular a blood velocity measuring system comprising a first, transmitting transducer in the form of a crystal and energized by a continuous wave generator to generate an ultrasonic signal of a frequency of 3.13 MHz. The ultrasonic signal is directed into a conduit through which blood is passed, the ultrasonic wave being reflected by the blood cells of the blood directed through the conduit, to be detected by a second or receiver transducer. The reflected ultrasonic wave is frequency-shifted dependent upon the velocity of the blood directed through the conduit. Subsequently, the signal derived from the second ultrasonic transducer is amplified and demodulated before being applied to a frequency-to-voltage converter, the amplitude of whose output provides an analog manifestation of the velocity or rate flow of the blood through the conduit.

It is desired to provide a liquid or blood velocity measuring apparatus that is adapted to measure velocity or rate flow of a liquid through any of a plurality of conduits. In this regard, it is understood that as the diameter or cross-section of a conduit is decreased, that, for a given flow of liquid, its velocity increases. Conversely, as the cross-sectional area of a conduit is increased, the velocity of the liquid is decreased, where there is a constant flow or quantity of liquid directed through the conduit.

Further, it is desired to provide a portable liquid velocity system that may be energized by a self-contained power source such as a battery. When using batteries, it is desired to minimize the energy drained therefrom in order to extend their life. In considering the use of batteries to energize a liquid velocity measuring system of the type described above, it is contemplated that the crystal-type transmitter and in particular the generator for energizing such a transmitter at a high frequency, imposes a large current drain on a battery. Thus, it is desired to only intermittently operate such systems in order to measure liquid velocity upon command of the system's operator. In one particular contemplated environment, a portable blood velocity measuring system could be used in a hospital, whereby an attendant would carry the blood velocity measuring system from patient to patient. In particular, the contemplated apparatus would be most suitable for measuring blood flow through a conduit of a dialysis machine or heart assist machine, and could be readily transported from one machine to the next.

In U.S. Pat. No. 3,741,014 of Tamura, there is described an ultrasonic current meter for measuring the flow rate of a fluid utilizing the Doppler phenomena. In particular it is contemplated that an oscillator or generator would energize an ultrasonic transmitter to direct an ultrasonic wave into a liquid, to be reflected by the liquid and received by a receiver transducer. The output of the receiver transducer is amplified and mixed with a signal as derived from the transducer oscillator or generator. In turn, the output of the mixer is applied subsequently to a detector and to a "signal pulse converter". The output of the converter comprises a train of signals proportional to the Doppler frequency and is multiplied by a scale factor and converted into a binary decimal code by the converter to provide a digital output signal that may be displayed by a digital indicator.

In U.S. Pat. No. 3,921,622 of Cole, there is described a system for transmitting a continuous ultrasonic signal across a conduit through which a fluid is directed to detect changes in the amplitude of the received signal, indicative of changes in its acoustic impedance and therefor the presence of bubbles within the liquid flow. If the impedance of the liquid increases above a predetermined level as determined by a trigger circuit, a clock circuit is connected to a counter, whereby the number of clock signals occurring after the detection of the bubbles is counted.

SUMMARY OF THE INVENTION

It is an object of this invention to provide a new and improved liquid velocity measuring system that may be calibrated to measure velocity flow through any of a number of conduits.

It is a further object of this invention to provide a new and improved velocity measuring apparatus that is adapted to be energized by a self-contained power source such as a battery, and, in particular, to reduce the energy drain upon the self-contained power source.

It is still a further object of this invention to provide a new and improved liquid velocity measuring system that is implemented by digital circuitry designed to minimize the power drain upon the self-contained power source.

In accordance with these and other objects, this invention is directed towards a liquid velocity measuring system comprising an actuatable generator for providing a relatively high frequency signal to a transmitting transducer for directing an ultrasonic wave into a conduit through which liquid is directed. A receiver transducer is disposed to receive the acoustical wave as reflected from the liquid, and to provide an output signal to be amplified and demodulated to provide a train of relatively low frequency pulses, the frequency of which is indicative of the velocity of the liquid directed through the conduit. The train of pulses is applied to a counter and a decoder for respectively counting and decoding the pulses to provide a signal to a suitable manifestation or display device, whereby an indication of the liquid velocity may be given. Further, a timing circuit is provided for enabling the counter and the decoder for a selected enabling or calibrating period of time, made dependent upon the cross-sectional area (or diameter) of the conduct through which the liquid is directed. It is understood that as the cross-sectional area of the conduct is decreased, for a given quantity or flow of liquid, the liquid velocity is increased and therefore, the counter enabling period is decreased. Conversely, as the cross-sectional area of the conduit is increased, the enabling period is increased.

In a further aspect of this invention, a timing-power circuit serves to energize, upon closing of a switch by the system's operator, at least the display device for a relatively longer system's operating period of time, and thereafter, for de-energizing the system. In an illustrative embodiment of this invention, the switch is closed to actuate the timing-power circuit and also to actuate a first one-shot multi-vibrator to establish a relatively short warm-up period, in which the elements of the digitized circuit are stabilized, and thereafter, for energizing a second one-shot multivibrator, whose period is variably set to establish the enabling period.

BRIEF DESCRIPTION OF THE DRAWINGS

These and other objects and advantages of the invention will become more apparent by referring to the following detailed description and accompanying drawings, in which.

DETAILED DESCRIPTION OF THE PREFERRED EMBODIMENTS

Figure 1:
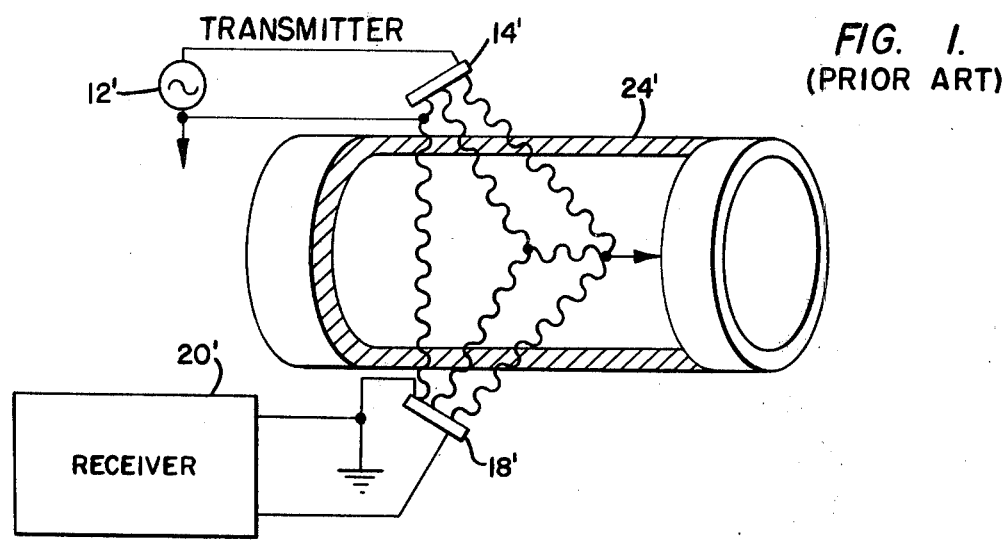
FIG. 1 is a description of a prior art transducer illustrating the general principles of a Doppler-type liquid flow measuring system.
Figure 2:
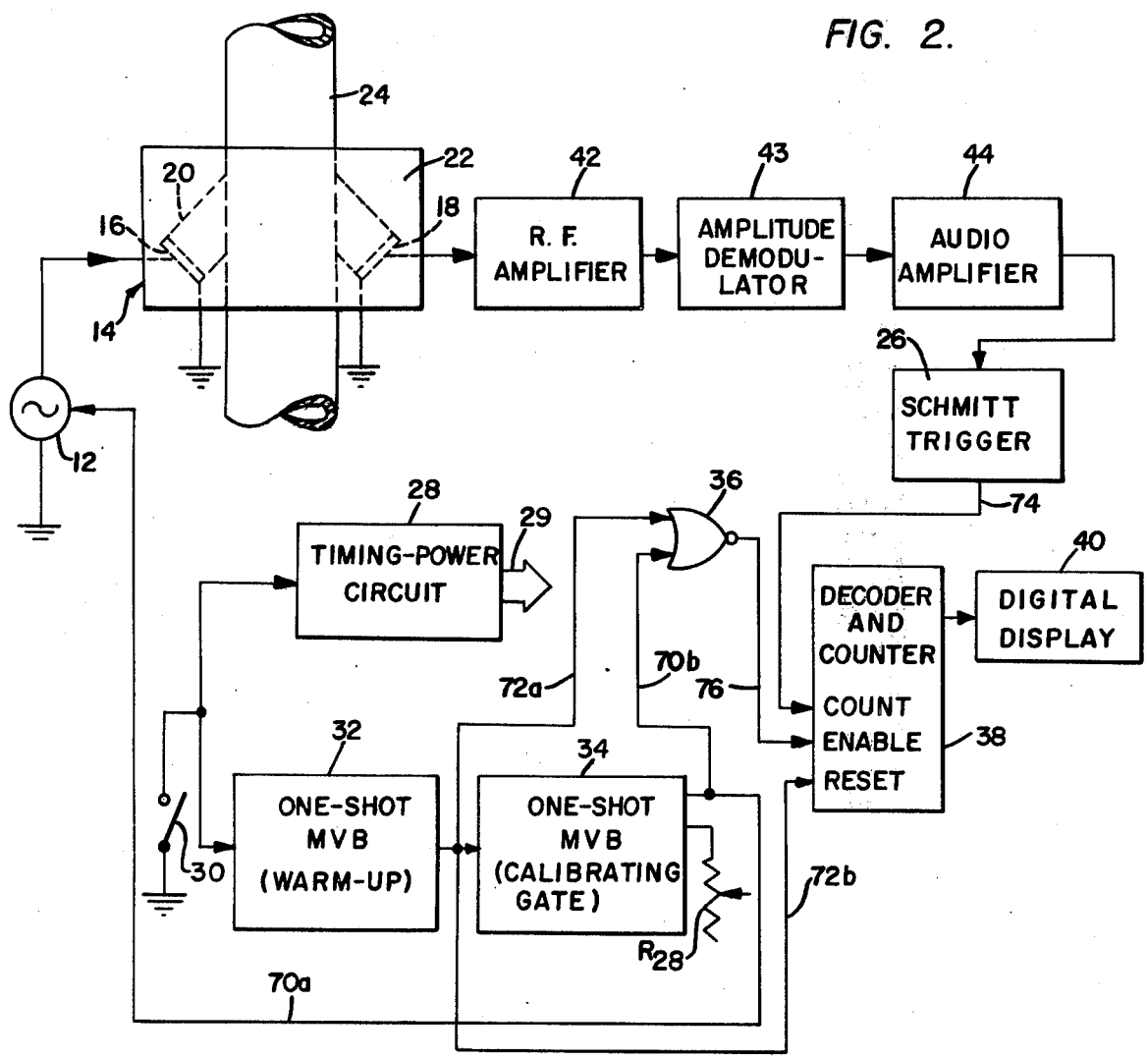
FIG. 2 is a functional block diagram of a system comprised of digital circuits, for measuring liquid velocity in accordance with the teachings of this invention; and, FIGS. 3A and B is a detailed schematic diagram of an illustrative embodiment of the velocity measuring system, as shown in FIG. 2.

With regard to the drawings and in particular to FIG. 2, there is shown a liquid velocity measuring system 10, including a continuous wave generator 12 for energizing a transmitting transducer 16 to emit energy in the form of ultrasonic waves toward and into the liquid, whose velocity is to be measured, as directed through a conduit 24 past transducer 16. Energy is reflected or scattered from the moving liquid to be detected by a receiver in the form of a crystal 18, which converts the transmitted ultrasonic waves into an electrical signal of a frequency in the order of 2-4 MHz that is applied to an RF amplifier 42, which is adapted to amplify signals of such frequencies and applies its amplified output to an amplitude demodulator circuit 43. The transmitter transducer and receiver transducer 16 and 18 are mounted about the conduit 24 by an assembly 14. The transducer assembly 14 includes the transmitting transducer 16 and the receiving transducer 18, each made of a lead titanium zirconate (LTZ) one-inch square that is cut to approximate dimensions of 0.290" square and mounted, respectively within the top housing 20 and the bottom housing 22 of the assembly 14. In an illustrative embodiment of this invention, the transmitting transducer 16 was selected to be LTZ-1 material with the receiving crystal 18 an LTZ-5, whereby the entire system sensitivity was improved by a factor of approximately 2 over an embodiment where the transmitting transducer 16 was also made of an LTZ-5 material. The demodulator circuit output is applied to an audio amplifier 44.

The envelope of the signal received by the crystal 18 represents the combination of the carrier of the transmitted energy or ultrasonic waves with the backscattered signal, whose normal frequency has been shifted by the Doppler phenomenon, in accordance with the velocity of the liquid directed through conduit 24. In essence, the demodulator 43 provides an output in accordance with the envelope of the received signal, which in turn is applied to the audio amplifier 44 to amplify the detected audio signal.

In an illustrative embodiment of this invention, the generator 12 is operated to generate an output frequency in the order of 3.13 MHz as a compromise between attenuation and resolution. It was found that as higher frequencies were used, attenuation was increased unduly, though resolution was improved. Thus, in the measurement of blood flow, red cells have a typical diameter of 8 micrometer and a thickness of 2 micrometer, so that the wavelength of the selected 3.13 MHz ultrasonic beam would be approximately 480 micrometer in blood. As a result, the red cells have a smaller diameter than the wavelength of the ultrasonic beam, and the red cell is set into motion, thus becoming a secondary emitter acting as a point source whereby energy is radiated toward the receiving crystal 18. Thus, the envelope of the electrical output signal provided by the crystal 18 represents the combination of the transmitted carrier signal as derived from the transmitting crystal 16 with the backscattered signal whose normal frequency has been shifted by the Doppler phenomenon. The receiving crystal converts the ultrasonic energy back into an electrical signal, which is amplitude modulated at microvolts level.

The detection amplification of the signal derived from the receiving crystal 18 presented various problems, one due primarily to the large range of amplitude of the signals derived from the crystal 18. In this regard, the amplifier 42 and the demodulator 43 are designed to handle a large dynamic range and, in an illustrative embodiment of this invention, are formed of discrete parts, as opposed to being formed of a single integrated circuit, to provide low noise amplification, capable of handling a gain of approximately $10^3$, without saturation. By using discrete components with a low noise preamplifier, a system gain may be obtained from the amplifier 42 and the amplifier 44 of about $10^5$ without at the same time making the noise produce false readout.

As shown in FIG. 2, the output as derived from the audio amplifier 44 is a series or train of pulse-like signals, the frequency of which is indicative of the velocity of the fluid directed through the circuit 24. The train of pulses is applied to a Schmitt trigger 26, which produces uniform amplitude output signals in a suitable condition to be counted to provide a digital indication of liquid velocity. The output of the Schmitt trigger 26 is applied to a decoder and counter 38 and in particular to its count input. The decoder and counter 38 operates to count number of pulses as applied during a calibrated or enabling period, as determined by the length or pulse width of a signal applied via conduit 76 to a latch enable input of the decoder and counter 38. Further, the decoder and counter 38 interprets or decodes the number of pulses to provide a digital output signal to be applied to a digital display 40, upon which is provided a digital representation of the velocity of the liquid directed through the conduit 24.

Further, there is provided suitable timing circuitry that is initiated by closing a start-up switch 30, whereby a timing-power circuit 28 is actuated for a predetermined, system's operating period sufficient to make a liquid velocity measurement of the liquid velocity and to display a digital manifestation thereof. Though not shown in FIG. 2, the timing-power circuit 28 includes a self-contained power source, e.g., a battery, that is selectively applied for the system's operating period. The timing-power circuit 28 is interconnected by connectors 29, only collectively shown in FIG. 2, to each of the remaining elements or circuits of the system shown in FIG. 2. In operation, the closing of the switch 30 actuates a first one-shot multi-vibrator (MVB) 32, which provides an output pulse-like signal of a predetermined, relatively short warm-up period in the order of 0.47 seconds to permit the system to stabilize before beginning a counting and measuring operation. In turn, the output of the one-shot MVB 32 is applied to a first input of a NOR gate 36, and also to reset the various components of the decoder and counter 38. After the warm-up period is established by the first one-shot MVB 32, a second one-shot multi-vibrator 34 energized by its output for a variable calibrating period of time determined by a potentiometer R28. The output of the second one-shot MVB 34 is applied via a conduit 70b to enable the NOR gate 36, whose output is applied via connector 76 to the enable input of the decoder and counter 38, enabling it for the calibrated period determined by the second one-shot MVB 34. Further, the output of the second one-shot MVB 34 is applied via connector 70a to actuate the generator 12 to apply a high frequency signal to the transmitting transducer 16, whereby a high frequency acoustical signal is transmitted into the circuit 24 to be reflected by the liquid and detected by the receiving transducer 18. The calibrating period as set by the one-shot MVB 34 is determined to be relatively short with respect to the system's operating period set by the timing-power circuit 28. As a result, the generator 12, which imposes a relatively high current drain, is energized by the self-contained power supply for the relatively short calibrating period, whereas the decoder and counter 38 and the digital display 40 are energized by timing-power circuit 28 (and its self-contained power source) for the relatively long system's operating period to permit the operator sufficient time to readily observe and record the liquid velocity as displayed by the display 40.

As explained above, the output of the receiving transducer 18 is successively amplified by the RF amplifier 42, demodulated by the amplitude demodulator 43, further amplified by the audio amplifier 44 to be applied to the Schmitt trigger 26 to provide a series or train of uniform amplitude pulses via the connector 74 to the count input of the decoder and counter 38. Thus, the timing circuit comprised of the elements 28, 32 and 34 serve to warm up or stabilize the various elements of the system and thereafter energize the transmitting transducer 16 for a relatively short time, i.e., the calibrating or enabling period, thereby tending to reduce the current or power drawn upon the battery as contained within the timing-power circuit 28. After the extended system's operating period has terminated, the timing-power circuit 28 disconnects the power as applied via the connectors 29 to the circuits or elements of the system shown in FIG. 2.

Figure 3A:
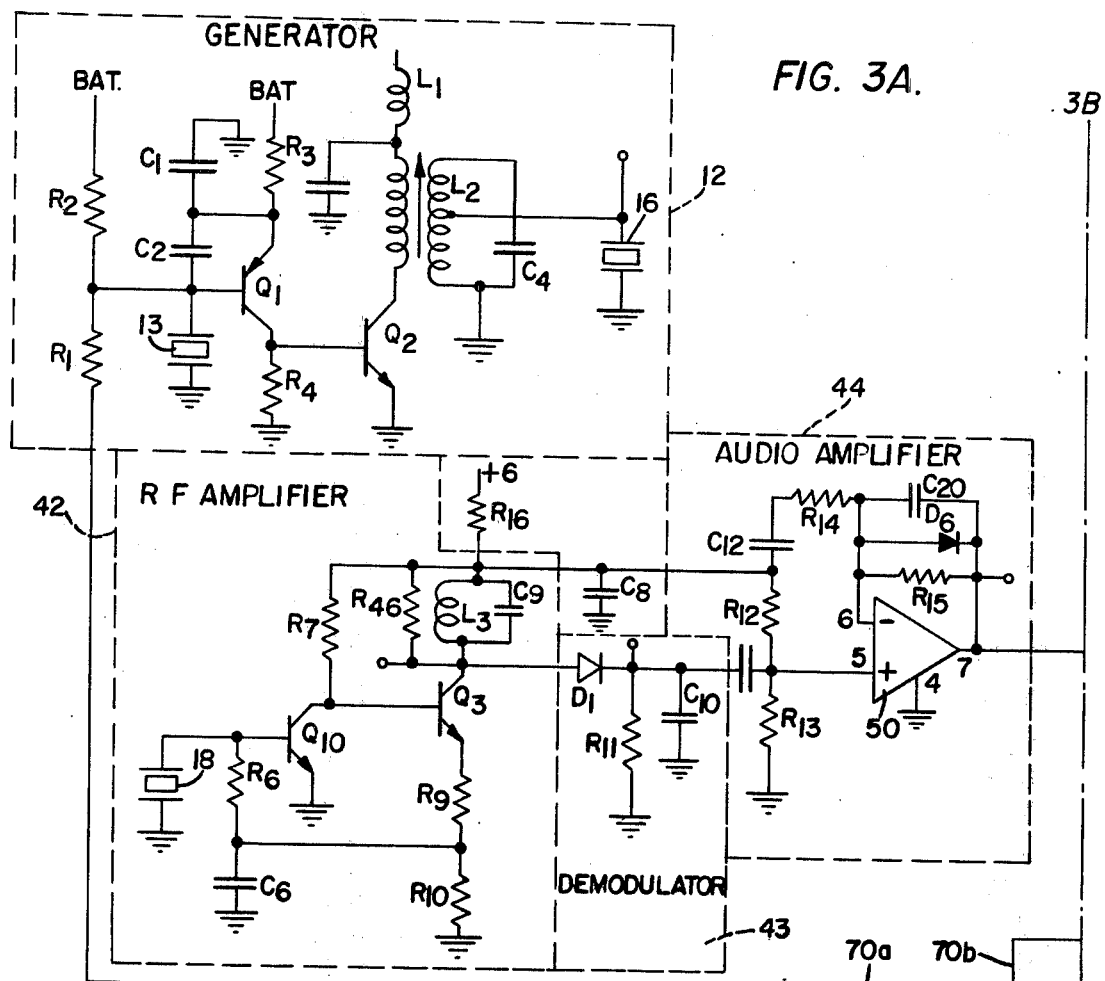
Figure 3A:
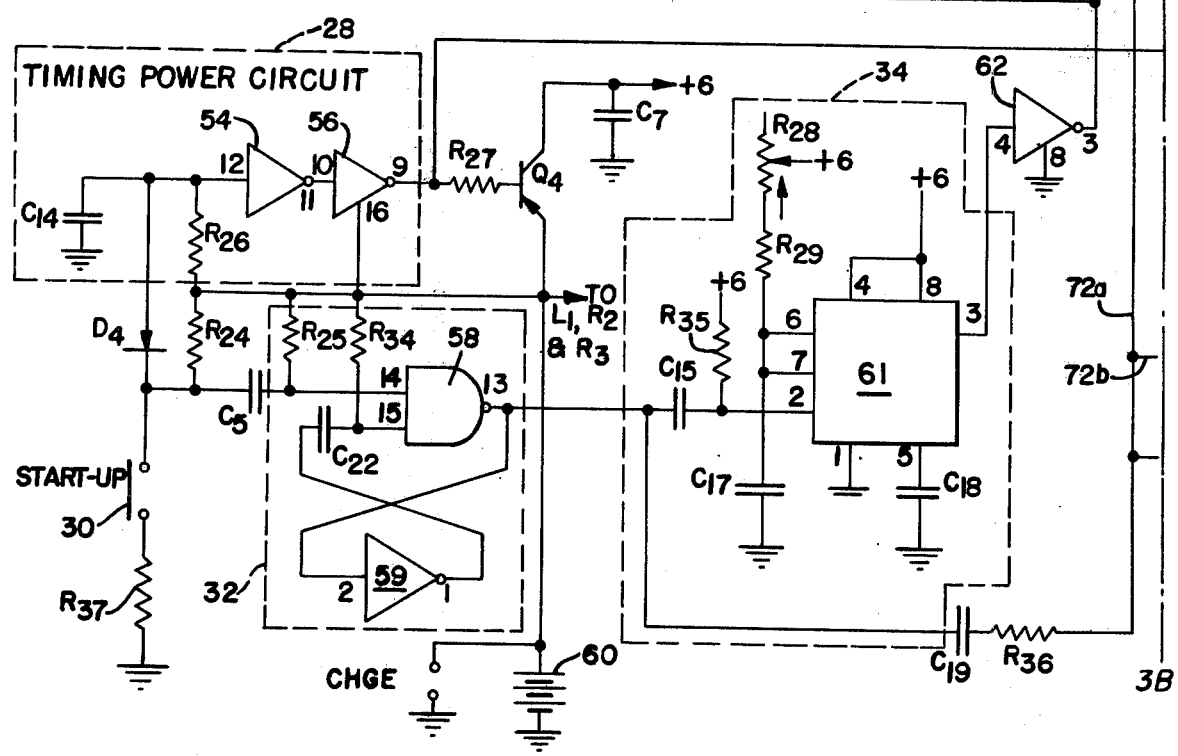

Referring now to FIGS. 3A and B, there is shown a detailed circuit schematic diagram of the system as shown in the functional block diagram of FIG. 2, with similar circuits being enclosed by dotted lines are identified by corresponding numerals. In its dormant condition, with the start-up switch 30 in its open position as shown in FIG. 3A, the capacitor C14 of the timing-power circuit 28 is charged by a voltage applied by the self-contained power source or battery 60, through the resistor R26. The potential stored by capacitor C14 is applied via logic gates 54 and 56 to the base of a transistor Q4, rendering it non-conductive and thus removing the system's operating voltage, e.g., six volts, from the remaining elements of system. As seen in FIGS. 3A and B, the +6 volts derived from the collector transistor Q4 is applied to various points throughout the remainder of the system. As a result, the battery 60 is conserved in that the drain imposed thereon by the elements of the system and in particular the generator 12 and its transmitting transducer 16, are effectively disconnected by switching means in the form of transistor Q4. Further, the high output of the second or calibrating one-shot MVB 34, as derived through an inverter 62 and the connector 70a is applied to generator 12 and in particular to the base of its transistor Q1, to render the transistor Q1 non-conductive to thereby disconnect the battery 60 that is directly applied to the various elements of the generator 12, as indicated in FIG. 3A. Further, as is apparent from FIGS. 3A and B, the various active elements such as the logic gates 54, 56 and 59, and the gate 58 of the timing-power circuit 28 are connected continuously to the battery 60, and are of C-MOS construction so that they draw low current from the battery 60.

Figure 3B:
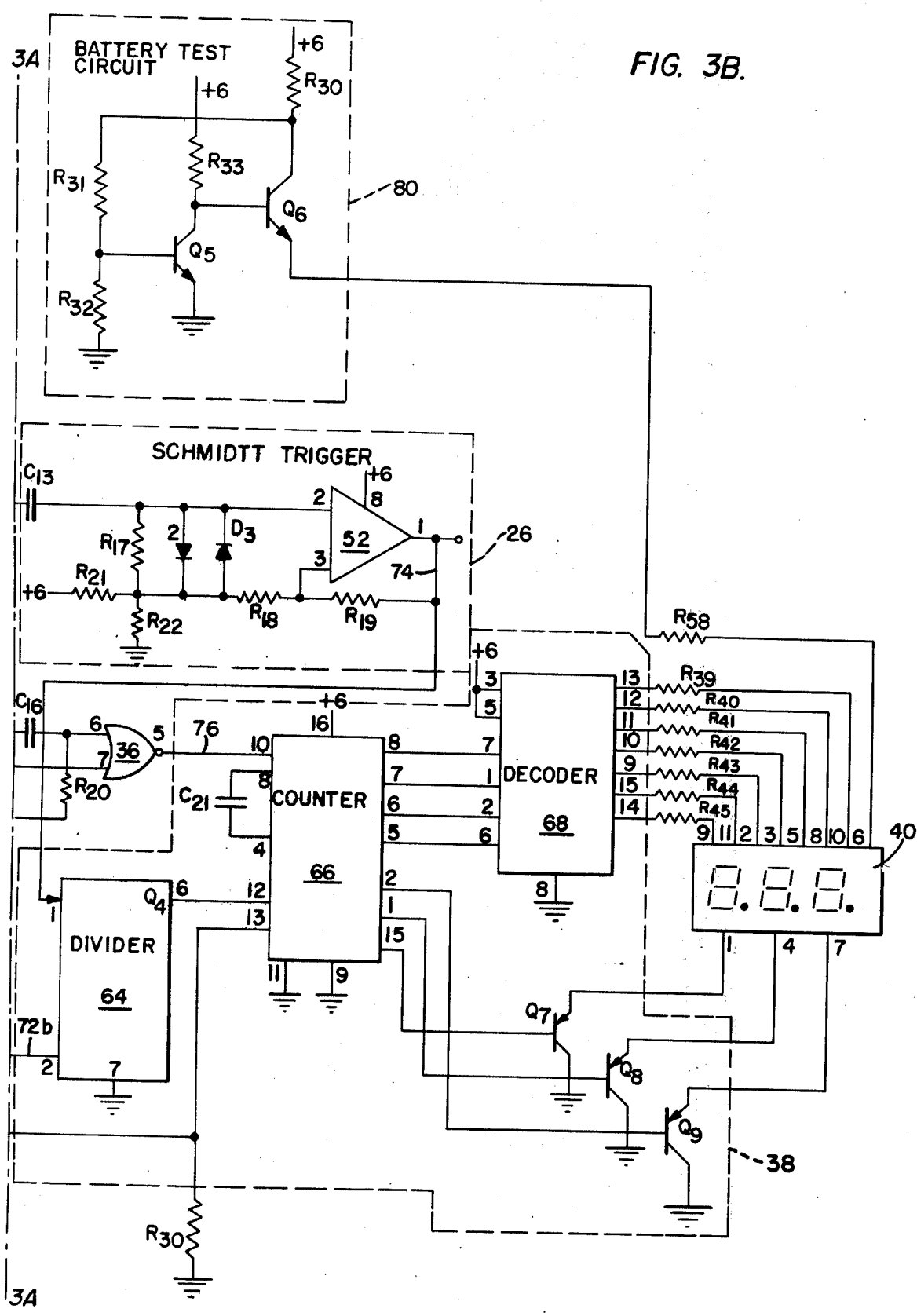

In order to initiate the operation of the velocity measuring system, the start-up switch 30 is closed, thereby discharging the capacitor C14 through diode D4 and resistor R37 to ground. The diode D4 serves to quickly discharge capacitor C14 to initiate the system's operating period as determined by the time constants of a charging circuit comprised of the capacitor C14, resistor R26 and the voltage of the battery 60. In other words, the battery 60 charges capacitor C14 through the resistor R26, the charging requiring a period corresponding to the system's operating period, e.g., 20 seconds, until the potential upon capacitor C14 is sufficient, as operated by logic gates 54 and 56, to turn "off" the transistor Q4, whereby the operating potential in the order of +6 volts is disconnected from the various elements of the system as shown in FIGS. 3A and 3B. It is understood that the system will remain energized for this period as determined by this timing or charging circuit and thereafter, be de-energized, thus to extend the life of the battery 60.

Also, upon closing the start-up switch 30, a pulse or spike is applied through capacitor C5 to the first or warm-up delay one-shot MVB 32 comprised of the gate 58 and logic gate 59. The output of the first one-shot MVB 32 is applied via connector 72b to reset the decoder and counter 38 and in particular to the reset inputs of its divider 64, and its counter 66. The one-shot MVB 32 provides a pulse-like output of a selected duration, e.g., 0.47 seconds, at the output 13 of the gate 58 to be applied to the second one-shot MVB 34 and via capacitor C19, resistor R36, and connector 72a to the input 7 of the NOR gate 36 (see FIG. 3B), thus latching the reset state of the counter 36 for the warm-up period.

The negative going edge of the output pulse from the first one-shot MVB 32 triggers the second or calibrating one-shot MVB 34 to be turned on for the enabling or calibrating period, as determined by a timing circuit comprised of the resistor R28, resistor 29 and capacitors C17. As indicated in both FIGS. 3A and B, and 2, the resistor R28 is a variable resistor that is set in accordance with the cross-sectional area or diameter of the conduit 24 through which the liquid or blood is directed. In this regard, as the diameter or cross-sectional area of the conduit 24 increases, the liquid velocity decreases for a given flow therethrough. Conversely, as the cross-sectional area of the conduit 24 decreases, the liquid velocity increases for a given flow. Thus, the enabling or calibrating period is increased as the cross-sectional area of the conduit 24 increases, to achieve as corresponding correct digital display upon the display 40 and conversely the calibrating, period is shortened as the cross-sectional area of the conduit 24 decreases and the resultant frequency of the signals as divided by divider 64 and applied to the counter 66 increases. In practice, the calibrating period is adjusted imperically by setting the resistor R28 for a particular conduit of a given cross-sectional area so that the liquid velocity indicated upon the display equals that indicated by a second, standard velocity measuring system. In an illustrative embodiment to this invention, wherein the conduit 24 has an outer diameter of ¼" and an inner diameter of 3/16" and the divider 64 divides by a factor of 16, the one-shot MVB 34 is set as by its resistor 28 to provide an output of a duration of approximately 3.5 seconds. In this regard, the resistor R28 may be set to provide outputs of periods in the range of 3 to 4.5 seconds. The setting of the calibrating period is effected imperically in that the conduit 24 may be made of a relatively flexible material and when it is disposed within the assembly 22, its configuration is no longer perfectly circular but is reshaped to be oblong.

The trailing edge of the positive going output pulse from the second one-shot MVB 34 is inverted by the inverter 62 and applied to the input 6 of the NOR gate 36, thus enabling NOR gate 36. As a result, the output derived from the terminal 5 of the NOR gate 36 goes low thus latching the count of counter 66 to display the count which occurred as the decoder and counter 38 counted the number of pulses derived from the Schmitt trigger 26. In an illustrative embodiment of this invention, the binary divider 64 may take the form of that divide-by-16 divider, as manufactured by Motorola under the designation 14024, the counter 66 may take the form of a three-stage decade BCD counter, as manufactured by Motorola under the designation MC14553, an the decoder 68 may take the form of a BCD-to-7 segment decoder/driver, as manufactured by the National Semiconductor Co. under the designation 74C48.

As shown in FIG. 3A, the output derived from the terminal 3 of the inverter 62 is applied via a connector 70a to turn on the generator 12 and in particular to render its transistor Q1 conductive whereby the voltage as derived from the battery 60 is applied to energize the generator or oscillator circuit 12, thus actuating the transmitter 16 to generate a corresponding acoustical wave into the conduit 24, as seen FIG. 2. The acoustical wave is reflected by the liquid flowing through the conduit 24 and is sensed by the receiving transducer 18 of the RF amplifier 42. The output of the receiver transducer 18 is successively amplified by the RF amplifier 42 comprised of transistors Q10 and Q3 and is applied to a demodulator or square law detector 43 which demodulates the amplified signal, detecting and applying its envelope to the audio amplifier 44, comprising an operational amplifier 50. As shown in FIG. 3B, the amplified output is in turn applied to the Schmitt trigger 26 comprised of an operational amplifier 52 that further processes the signal to provide a series or train of uniform amplitude output signals whose frequency is indicative of the liquid directed through conduit 24. As indicated above, the train of processed pulses derived from the Schmitt trigger 26 is applied to the binary divider 64 to be divided by a factor of 16 related to the sampling or calibrating period to transform the frequency of the Schmitt trigger output to a digital rate. The output of the binary divider 64 is applied to the count input of the counter 66, which counts the divided input over the sampling or calibrating period, that has been dependent upon the cross-sectional area of the conduit 24. At the end of the calibrating period, the output 5 of the NOR 36 goes low latching the count of counter 66.

It is understood that the calibrated or enabled period is relatively short with respect to the system operating period, e.g., 20 seconds, so that after the counting has taken place by the counter 66, the display continues for a relatively long period of time. In this regard, the timing-power circuit 28 remains on to apply its +6 volts to the elements of the circuit and in particular to the binary divider 64, the counter 66, a decoder 68 and the digital display 40, thus permitting the continued display of the liquid velocity. The decoder 68 decodes the binary count as derived from the counter 66 and drives three-digit digital display 40 with a series of single-digit decimal numbers. The counter 66 also functions as a time multiplexer applying timing signals via each of the transistors Q7, Q8 and Q9 to energize a corresponding input 1, 4 and 7 of the display 40 so that the corresponding decimal numeral as derived from the decoder 68, is displayed in the correct order and by the correct digit of the display 40.

In a further feature, if the start-up switch 30 is re-closed, even during an extended display period, the system as shown in FIGS. 3A and B is capable of taking an updated reading. This is possible due to the operation of the diode D4 to discharge rapidly the capacitor C14 to re-initiate the next system operating period. Without the incorporation of the diode D4, the discharge of the capacitor C14 will be relatively slow requiring the operator to wait for an extended length of time until an update could be initiated.

The battery 60 may be of a rechargeble type and its voltage is applied by the collector of transistor Q4 to a battery test circuit 80 comprised of voltage sensing transistors Q5 and Q6. Thus, if the voltage of the rechargeable battery 60 falls below a predetermined level indicating that recharging is required, an output signal is derived from the emitter of transistor Q6 and applied to the input 6 of the digital display 40, whereby the decimal points associated with each of the digits are energized, thus indicating to the operator that battery 60 needs recharging.

Numerous changes may be made in the above-described apparatus and different embodiments of the invention may be made without departing from the spirit thereof; therefore, it is intended that all matter contained in the foregoing description and the accompanying drawings shall be interpreted as illustrative and not in a limiting sense.

We claim:

1. An ultrasonic wave system for measuring the velocity of a liquid flowing through a conduit, said system comprising:
   (a) first and second transducer elements operatively associated with the conduit respectively for transmitting an ultrasonic wave into the liquid flowing through the conduit and for receiving an ultrasonic wave backscattered by the liquid directed through the conduit;
   (b) a selectively actuatable generator means for applying a high frequency signal to said first transducer element causing it to emit the ultrasonic wave into the liquid;
   (c) said second electro-acoustical transducer element providing an electrical output signal of a frequency shifted from that high frequency of said generator means by the Doppler phenomenon, dependent upon the velocity of the liquid directed through the conduit;
   (d) first means coupled to receive the electrical output of said second transducer for providing an amplitude demodulated output signal;
   (e) second means responsive to the amplitude demodulated output signal of said first means for providing and displaying an indication of the velocity of the liquid flowing through the conduit; and
   (f) timing control means for selectively actuating for a first, relatively short period said generator means to apply its high frequency signal to said first transducer element, and for actuating for a second, relatively long period of time said second means to permit the continued display of the measured liquid velocity for said second period.

2. The system as claimed in claim 1, wherein there is included a self-contained power source, and said timing control means comprises a charging circuit including a resistor and a capacitor coupled to be charged by said self-contained power source.

3. The system as claimed in claim 1, wherein is included a self-contained power source, and said timing control means comprises an actuatable switch for initiating upon its closing said second period whereby said self-contained power source is applied to the elements of said system, and a third, warm-up period to permit the stabilization of the elements of the said system, before initiating said first period.

* * * * *